United States Patent [19]

Balslev et al.

[11] 4,438,100

[45] Mar. 20, 1984

[54] STERILIZED PRESERVED, STABLE MUCINE-CONTAINING SOLUTIONS

[75] Inventors: Erik Balslev, Fredensborg; Svenn S. Hansen, Virum; Ernst L. Pedersen, Taastrup, all of Denmark

[73] Assignee: A/S Orthana Kemisk Fabrik, Kastrup, Denmark

[21] Appl. No.: 336,357

[22] PCT Filed: Apr. 27, 1981

[86] PCT No.: PCT/DK81/00043

§ 371 Date: Dec. 28, 1981

§ 102(e) Date: Dec. 28, 1981

[87] PCT Pub. No.: WO81/02977

PCT Pub. Date: Oct. 29, 1981

[30] Foreign Application Priority Data

Apr. 25, 1980 [DK] Denmark .......................... 1811/80
Mar. 13, 1981 [DK] Denmark .......................... 1163/81

[51] Int. Cl.³ .................... A61K 35/38; A61K 33/40
[52] U.S. Cl. ................................... 424/104; 424/130
[58] Field of Search ............................... 424/104, 130

[56] References Cited

U.S. PATENT DOCUMENTS 2,276,882  3/1942  Schneiderwirth .................. 424/104
3,567,821  3/1971  Nouvel .............................. 424/104

OTHER PUBLICATIONS

Rokos et al.—Chem. Abst., vol. 64 (1966) p. 5625h.
Sizer—Chem. Abst., vol. 44 (1950) p. 10,002d.

*Primary Examiner*—Sam Rosen
*Attorney, Agent, or Firm*—Cushman, Darby & Cushman

[57] ABSTRACT

Sterilized, preserved, stable mucine-containing solutions for use for application to sensitive human mucous membranes of the oral cavity, the nasal system, and the eye ephithel contain an oxidizing bactericide, in particular hydrogen peroxide, as preservative. Even at very small hydrogen peroxide concentrations, solutions remain bactericidal over prolonged periods such as 1-2 years. Mucine used is porcine gastric mucine or bovine salivary mucine or—to adjust the polar/non-polar properties—a mixture of both.

The pronounced lubricating effect, combined with suitable viscosity, low surface tension and ability to coat and protect mucous membranes renders the solutions well suited as artificial salivas, ophthalmic solutions, and carriers for medicaments.

29 Claims, No Drawings

STERILIZED PRESERVED, STABLE MUCINE-CONTAINING SOLUTIONS

The present invention relates to sterilized, preserved, stable mucine-containing compositions and methods for their preparation.

The compositions of the present invention, which are in particular aqeuous solutions (colloid solutions), utilize unique advantageous properties of mucines, especially particular kinds of mucines described below, and relate to sterilized solutions of mucine, in particular for a number of applications where the special nature of glycoproteins—together with the fact that glycoproteins constitute natural products which are extracted from animals and which, with respect to their properties, are closely related to the properties of the glycoprotein solutions secreted in the human system—has been found to be particularly beneficial. In all of the applications contemplated, special properties of mucines—including viscosity properties, surface active properties, polar/non-polar properties, lubrication properties, and ability to be effectively sterilized and preserved and even imparted bactericidal properties and to resist enzymatic degradation without to any substantial degree loosing their valuable properties—render the solutions of the invention particularly well suited for direct or indirect application to sensitive human mucous membranes such as the mucous membranes of the oral cavity, the nasal system, and the eye epithel.

Thus, the solutions of the invention are, in particular, adapted for oral or nasal administration to human beings, or for closely related applications, such as for use as ophthalmic solutions. For these purposes, the solutions should be sterilized and should contain a preservative so that they will maintain sterility even when exposed to a certain contamination during storage and application.

Hence, one of the main aspects of the invention is constituted by aqueous muchine-containing compositions, in particular for application to human mucous membranes and/or for use as an ophthalmic solution, comprising a non-human mammalian mucine selected from the group consisting of buccal and gastrointestinal mucines, the composition having a viscosity of at the most 50 relative to water, as measured with an Oswald viscosimeter, said composition being sterilized and containing a preservative which is present in a physiologically tolerable concentration with respect to the application of the composition.

One of the main utilities of this aspect of the present invention is constituted by solutions for oral administration to human beings. This aspect will now be dealt with in greater detail:

It is well-known that dryness of the mouth is a frequently occurring condition. The dryness may vary from slight dryness with transitory inconvenience to a total xerostomia with severe concomitant symptoms (problems in connection with speech, mastication, swallowing, digestion and physical and psychic indisposition) and serious consequences for the buccal cavity of the patient (destruction of the teeth because of carial and/or marginal parodontite), fungal infection and a very sensitive mucous membrane with consequent difficulties in accepting dentures.

The reasons for mouth dryness may be physiological (age, menopause, postoperative conditions, dehydration), psychic (nervousness), pharmacological (anticholinergica, anti-histaminica, anti-hypertensiva, sedativa and neuroleptica) and radiotherapeutic (after irradiation of tumours on head and neck). Especially irradiation drastically reduces the normal saliva secretion.

Normally, human beings have a salivary secretion varying between 1000 and 1500 ml in the course of 24 hours. This secretion is a mixture of scretions from the submandibular, sublingual, and parotidal glands. More than 98% of the mixed salivary secretion is water, 0–3% is constituted by organic substances, and about 0.25% are inorganic substances.

Among the inorganic and organic components of the natural salivary secretion, a number of substances are not normally taken together with the daily food, and therefore, deficiencies may occur in the organism if they are not supplied in another manner. The following are examples of substances, the importance of which is partially known. (The substances are listed on the basis of 1 liter of salivary secretion per day).

KSCN: 0.25 g
Mucine: 0.5–1.0 g
  (mucoprotein, including bound carbohydrates) including bound hexosamines: 0.05–0.1 g
  including bound sialic acid: 0.02–0.03 g
Enzymes:
  including amylase: 0.4 g
  and lysozyme: 0.10–0.15 g The thiocyanate constitutes part of an antibacterial system together with lactoperoxidase (an enzyme which is also present in salivary secretion) and hydrogen peroxide which is formed in small amounts in some of the bacteria of the mouth. On oxidation with hydrogen peroxide, thiocyanate is converted into a bacteriostatically active substance (hypothiocyanite). This oxidation process is catalyzed by lactoperoxidase, but proceeds slowly even without the presence of this enzyme.

Hence, a deficiency in thiocyanate as a consequence of lack of salivary secreation is a possible reason for fungal growth, e.g., on the tongue. Such fungal growth on the tongue is a well-known problem with patients suffering from xerostomia.

The mucine in the salivary secretion possesses several important properties which are essential to the properties of the saliva. Some of the most important properties of the mucine are as follows:

A lubricating effect. The food is easily swallowed, speaking is no problem, and there is no unpleasantness from dry mucous membranes.

The mucine makes the saliva sufficiently viscous to remain on the mucous membranes, and to move slowly on the mucous membranes and act as a carrier for other substances.

The mucine has surfactant effect and, hence, reduces the surface tension of the saliva to considerably below the surface tension of water, which contributes to make the saliva "foam" and act as an emulsifier for the food intake, to enable the saliva to distribute evenly over dry mucous membranes, and to mix freely with saliva already present.

From the above explanation of the characteristics of salivary secretion and the problems which occur when the salivary secretion is deficient, it will be understood that it would be most desirable to have an artificial saliva composition for human use, to relieve the above-mentioned inconveniences incurred by xerostomia or by a greater or lesser tendency to dryness of the mouth.

The ideal saliva composition should have physical and clinical properties which are as close to the properties of the mixed natural salivary secretion as possible. In contrast to the natural saliva in the mouth, it should be stable when stored and applied in liquid form.

As it is complicated in practice to apply the amounts corresponding to normal saliva secretion, that is, about 1-1.5 liters, of artificial saliva during a day and night in an automatic and handy way, the ideal artificial saliva should be based on intake of only 25-50 ml per day in a more concentrated form, but on the other hand combined with the intake of a relatively larger amount of water during the day, especially during meals and before sleeping.

Furthermore, for practical reasons, the ideal artificial saliva composition should be inhibitory to bacterial growth to such an extent that it can be used in refill systems, e.g., for storage during a longer period in a ½ liter bottle from which portions of the composition are withdrawn under non-sterile conditions at intervals and are transferred to a more handy container, e.g., a 25 ml vial, such as a plastic container, which may easily be kept in a pocket or small bag, and from which suitable portions can be taken by suctioning or sucking.

Besides the traditional household remedies such as gruel, glycerine, etc., the most used known artificial saliva compositions are based on carboxymethylcellulose as the medium which imparts, to the saliva composition, its lubricating effect and the necessary viscosity. Such a composition is described by J. Matzker in Z. Laryng. Rhinol. 51, 422-428 (1972) and contains 10 g of carboxymethylcellulose per liter, 30 g of sorbitol per liter, and small amounts of dissolved salts (potassium chloride, sodium chloride, magnesium chloride, calcium chloride, potassium hydrogen phosphate, and potassium thiocyanate).

The composition of this known artificial saliva is close to the composition of natural unstimulated saliva, apart from the essential components constituted by carboxymethylcellulose and sorbitol which have been added to impart lubricating and viscous properties to the saliva.

This known artificial saliva, and similar compositions, are widely used. They are nearly all based on sodium carboxymethylcellulose (in the following termed "carboxymethylcellulose" for brevity) and sorbitol and are preserved with methyl-p-hydroxybenzoate or other bactericidally and/or fungicidally active synthetic organic compounds.

Unfortunately, these known artificial saliva compositions suffer from the disadvantage that patients using them complain about sticky accumulations at particular sites in the mouth. Under these layers, irritation of the mucosa has been observed. Many patients complaint of unpleasant taste and of the fact that the lubricating effect in the mouth is of relative short duration.

One reason for these disadvantages may be that the essential component of the composition, carboxymethylcellulose, which comprises a different molecular structure from the molecules of the mucoproteins occurring in natural saliva, results in a high viscosity of the artificial saliva and a relatively high surface tension which by no means approaches the low surface tension of the natural saliva. Thus it has been found that the surface tension of compositions containing 1% by weight of carboxymethylcellulose together with 3% by weight of sorbitol is in the range of 60-65 dyn.cm whereas the surface tension of natural saliva is in the range of 48-53 dyn.cm.

Another reason for the disadvantages of the known artificial saliva compositions may be that the preservatives used therein differ very much from substances normally occurring in the saliva and hence may irritate the oral mucous membranes, in particular when their concentration increases with evaporation of the water of the composition. Also, the preservatives used in known artificial saliva compositions, even the above-mentioned methyl p-hydroxybenzoate which is most widely used for this purpose, has an unpleasant taste in high concentrations.

In 1974 it was shown that an artificial saliva containing 1% of mucine prepared from bovine salivary glands is preferred by patients suffering from xerostomia, over saliva compositions based on carboxymethylcellulose, as the mucine-containing composition had a better taste and remained in the mouth for a longer period, (E. J. 's-Gravenmade et al., Int. J. Oral. Surg. 1974:3, 435-439).

The artificial saliva compositions used for the experiments were prepared by dissolving 100 mg of lyophilized bovine salivary mucine exract in 10 ml of water. None of the solutions were used for more than 2 days at room temperature. Although the bacterial count for the artificial saliva composition has been low immediately after its preparation, there is no doubt that a longer term storage thereof at room temperature or in a refrigerator would result in a considerable increase in the bacterial count. Furthermore, it was not easy to obtain a sufficiently homogeneous solution of the mucine, as an ordinary stirring into water by the user is relatively time-consuming and yields a varying result. A non-homogeneous solution, when taken, can result in varying deposits of the mucine on the mucous membrane, which is inexpedient.

The present invention provides an artificial saliva composition, and, in a broader sense, a composition for oral administration to human beings, which is not associated with any of the above-mentioned drawbacks, and which conforms to the characteristics of an ideal artificial saliva composition.

The composition of the invention containing a non-human mammalian mucine selected from the group consisting of buccal and gastrointestinal mucines has a low bacterial count obtained by sterilization and by means of a preservative incorporated in the composition. The composition of the invention is preferably substantially free from any mucine-decomposing enzymatic activity.

In the present specification and claims, the term "preservative" is intended to designate a substance showing antimicrobial properties, in particular bactericidal properties and preferably also antifungal properties. As will appear from the following description, oxidizing bactericides, including peroxides and in particular hydrogen peroxide, are preferred preservatives for the purpose of the present invention.

As will be understood, the composition, when ready for use, will contain the mucine in aqueous solution (or, expressed more correctly, in aqeuous colloid solution), but it is within the scope of the invention to supply the composition in the form of a dry formulation, e.g. a powder or granulate, for reconstitution before use.

Due to the low bacterial count (usually as low as at the most 10 bacteria per gram of the composition), the composition will, in practice, be free from any bacterial degradation or contamination. Due to the freedom from any mucine-decomposing enzymatic activity, the composition will be substantially free from any enzymatic degradation of the mucine.

In the present context, the term "buccal and gastrointestinal mucines" is intended to designate any mucine which is present in the oral cavity or in the gastrointestinal system. Typical examples are mucines from salivary glands and gastric mucines.

As stated above, a low bacterial count, typically of at the most 10 per gram, in the composition of the invention is obtained by means of a preservative. The preservative (or combinations of preservatives) having bactericidal and, preferably, also fungicidal properties may be present in the final composition, or may be included in the preparation of the composition in such a way that it is substantially no longer present in the final composition, or it may be both included in the preparation of the composition and added in such a way that it is present in the final composition, such as will be understood from the more detailed explanation to follow.

When medicaments or other agents for human oral administration are sterilized, this is normally performed, e.g., by an autoclave treatment or by filtration through a sterile filter. If it were attempted to sterilize mucine-containing compositions by autoclave treatment, the viscosity of the mucine would degrade drastically, which in practice would make the mucine less applicable for the purpose of the invention. Furthermore, a filtration of the mucine-containing composition through a sterilizing filter is difficult. More importantly, however, none of these methods of sterilization contribute to any preservation of the product.

Therefore, the obtainment of sterility by means of a preservative in accordance with the present invention is a very important feature characterizing the process and the product of the invention.

As stated above, the composition of the invention contains a preservative, in order to secure that it will remain free of bacterial growth even if it is not stored and handled under sterile conditions. On the other hand, if the bacterial count of an artificial saliva composition of the mucine-containing type according to the present invention has been lowered to at the most 10 per gram by treatment with a preservative during the preparation of the composition, and the composition is kept under sterile conditions, it might not be necessary that the composition still contains any preservative, but it is, nevertheless, always preferred according to the present invention that the composition contains a preservative.

The composition of the invention has preferably been treated and/or admixed with preservative to such an extent that its bacterial count remains substantially constant for a period of at least one year when the composition is kept in a closed container at room temperature, and more preferably, to such an extent that the bacterial count of the composition remains substantially constant when the composition is kept at 4° C. for a period of two months with occasional withdrawal of a portion of the composition, typically daily withdrawal of a portion of the composition.

Under the same conditions and during the same periods as stated above in connection with the bacterial count, the viscosity of the composition, when it is an aqueous solution, should preferably be stable to such an extent that it does not decrease to below 2, relative to water. This is obtained when any mucine-decomposing enzymatic activity has been substantially removed from the composition, and any preservative or preservatives present, and the concentration thereof, are suitably selected.

According to the invention, it has been found that an ideal preservative for the obtainment of the above-mentioned critical stability properties is an oxidizing bactericide. Examples of known oxidizing bactericides are ozone and peroxides, in particular hydrogen peroxide. Hydrogen peroxide serves both as a means to eliminate mucine-decomposing enzymatic activity, and as an efficient microbiocidal agent. According to the invention, it has been found that in the combination with the mucine, hydrogen peroxide, even in very low concentration, is surprisingly effective as a bactericide. Hydrogen peroxide may be used for treating the mucine material used in the composition of the invention prior to incorporating the mucine material into the composition, or for addition to the composition, or both. When hydrogen peroxide is present in the composition, it will not only serve as a preservative to keep the composition free from microbial growth when the composition is exposed to bacterial and fungal contamination, but will also impart a most desirable "freshness" to the composition. Furthermore, hydrogen peroxide will contribute to the natural bacterial and fungal balance of the oral cavity, since hydrogen peroxide plays an important role in this regard under the normal conditions prevailing in natural saliva secretion conditions. In this regard, and in other regards as will be explained below, hydrogen peroxide is preferred over other microbiocidal preservatives which can be administered to the oral cavity of human beings and which could therefore also be used for the purpose of the present invention but which have an unpleasant tast in the necessary concentrations thereof, such as chlorohexidine and methyl p-oxybenzoate.

According to the invention, the oxidizing bactericide is preferably present in the composition in a concentration of about 0.01–70 millimol per liter, such as 0.1–70 millimol per liter, in particular 0.05–20 millimol per liter, such as 0.5–10 millimol per liter.

When the oxidizing bactericide is hydrogen peroxide, a typical initial concentration thereof is about 10 millimol per liter.

The oxidizing bactericides, in particular exemplified by ozone and hydrogen peroxide, are active in extremely small concentrations. Thus, remarkable antibacterial and anti-fungus effects have been noted in the compositions of the present invention even long time after the concentration of oxidizing bactericide has decreased, during storage, to nearly zero.

Thus, e.g., when 600 ppm of hydrogen peroxide is added to a mucine-containing solution in the sterilization treatment, the hydrogen peroxide concentration will, after a few weeks, drop to about 300 ppm, after half a year to 50–100 ppm, and after one year, the concentration will be only slightly above zero. With ozone, the concentration will decrease more rapidly, from, e.g., 1 mg/liter to close to zero in a few hours.

Thus, it is characteristic to the sterilization and preservation with these oxidizing bactericides that the relatively high initial concentration thereof used in the sterilization process decreases rapidly during the initial short period whereafter a physiologically tolerable, but still bactericidally effective concentration is retained during the following storage and application period.

In a particular embodiment, the composition of the invention also contains other constituents which may serve to substitute saliva constituents, such as ion species found in human saliva, typically one or several ions selected from the group consisting of sodium, potassium, chloride, calcium, phosphate, magnesium, bicarbonate, and thiocyanate.

According to a preferred feature of the invention, the composition contains a thiocyanate, typically in a concentration of from 0.25 mM to 6 mM, in particular from 0.5 mM to 2 mM. Thiocyanates have a certain antimicrobial activity which is, of course, a desired property in the composition of the invention, but more important, thiocyanate is a constituent of human natural saliva and, as explained above, constitutes part of an antibacterial system comprising thiocyanate, hydrogen peroxide, and lactoperoxidase. When hydrogen peroxide and thiocyanate are present in the composition of the invention, such as is preferred, two components of this system are supplied by the composition. The third component of the system, lactoperoxidase, is present in any salivary secretion with which the patient may be able to contribute, or can be supplied from, e.g., milk which the patient drinks. Another interesting possibility is to include, in the composition of the invention, a system which will generate hydrogen peroxide in situ in the composition for balanced co-operation with the thiocyanate, e.g., a system comprising enzymes which, in the mouth, together with polysaccharides from the food generate hydrogen peroxide, such as a combination of amyloglucosidase and glucoseoxidase.

The composition of the invention may also contain fluoride ions, e.g. incorporated as sodium fluoride, in order to obtain a rehardening effect on dental enamel. When sodium fluoride is incorporated in the composition, it is normally incorporated in an amount of, e.g., 0.5–5 ppm, preferably 2 ppm.

The artificial saliva composition of the invention is preferably made with such a viscosity that the mucine thereof will remain as a protective coating on the surfaces of the mouth for a sufficiently long period. For practical reasons, it is desirable that the necessary doses of the artificial saliva are relatively small so that the patient can easily carry a small container containing the necessary volume for a period of e.g., one day and night, typically a volume of 25–50 ml, which means that suitable doses should be about 1–2 ml. When supplied from such small volume doses, the mucine of the composition should be capable of substantially substituting for the deficient saliva excretion. A suitable viscosity to obtain this is a viscosity of between 2 and 30 relative to water, as measured with an Oswald viscosimeter, preferably a viscosity between 4 and 10, in particular between 5 and 8. The suitable viscosity of the solution may be obtained by proper selection of the mucine, the pretreatment of the mucine, and the concentration of the mucine. It is within the scope of the invention to include, in the composition, other viscosity-imparting constituents than mucine. For example, one possibility that could be of interest would be to combine the mucine with a carbohydrate which is viscous in aqueous solution, such as carboxymethylcellulose.

According to the invention, it has surprisingly been found that a most desirable mucine for use in the composition is gastric mucine. In spite of its gastric origin, gastric mucine has been found, in practice, to function excellently as the mucine component of artificial saliva compositions. Porcine and bovine gastric mucine may be obtained on industrial scale at reasonable cost, and hence provide realistic mucine sources for artificial saliva compositions. Of course, gastric mucine could be combined with carboxymethylcellulose and/or with other mucines such as bovine salivary mucine. According to a particular aspect of the invention, compositions containing a combination of gastric mucine and bovine salivary mucine offer important advantages as artificial saliva compositions, such as is explained in greater detail below. In the following, porcine gastric mucine, which is an excellent mucine for the purpose of the present invention, will be dealt with in greater detail, but it will be understood that also other mammalian gastric mucines, in particular bovine gastric mucine, are valuable mucines for the purpose of the invention.

When porcine gastric mucine is used as the mucine component of the composition, it should be included in an amount corresponding to 0.2–6% by weight, typically 0.5–6% by weight, calculated on the mucine solution. Normally, the preferred concentration of the porcine gastric mucine is 1–4% by weight, calculated on the solution, but a slightly higher concentration, such as 2–5% by weight, may also be of particular interest.

Porcine gastric mucine is obtainable as a by-product in the production of pepsin from hog stomachs. When porcine gastric mucine is to be used for the purpose of the present invention, it is suitably prepared in a more pure form than the one normally produced. Such additional purification may be obtained by several alcohol precipitations, such as 2–3 precipitations with 60% ethanol. During the precipitations, and during the manipulation of the mucine, the use of gentle conditions will result in minimizing of viscosity-decreasing degradation. The purification is typically performed to such an extent that the mucine is substantially free of any peptone content. Thereafter, the resulting mucine is suitably treated with a preservative and dried, e.g. by spray drying. When the drying is performed by spray-drying, shelf-drying, or freeze-drying, it is preferred that the preservative be a low molecular weight volatile preservative such as hydrogen peroxide, which is suitably added to the mucine-containing solution to a concentration corresponding to about 0.01–0.2, suitably about 0.02–0.06, percent by weight. After the addition of the hydrogen peroxide, and prior to the spray-drying, the solution is suitably allowed to stand for a period between an hour and a few hours, typically about two hours, at room temperature. It has been found that this treatment will not only result in a material which is free of bacteria (has a bacterial count of at the most 10 per gram), but will also serve to remove any reminiscent bad taste from traces of peptones and fat. The spray-drying should be performed under conditions which are non-severe, a typical example of a preferred air inlet temperature being in the range of 150°–240° C., typically around 200° C., and the outlet temperature being in the range of 90°–180° C., typically about 150° C.

The above-mentioned conditions with respect to precipitation, addition of hydrogen peroxide and drying, are applicable also to other types of mammalian buccal and gastrointestinal mucines, including bovine gastric mucine and bovine and porcine salivary mucines.

Bovine salivary mucine may be obtained, e.g., as described by E. J. 's-Gravenmade et al,. Int. J. Oral Surg., 1974:3, 435–439.

When the drying is performed according to the above methods, the mucine-containing solution is preferably sterilized prior to drying, e.g. by adding a preservative.

The preferred preservative is hydrogen peroxide added in a concentration of 0.02–0.06 percent by weight.

The dried mucine preparation, in the form of a powder or a granulate having a bacterial count of less than 10 per gram, constitutes, in itself, a valuable composition of the invention. This composition can be shipped and stored under conditions which will retain its low bacterial count, and can then be reconstituted with water by the end user. Any added constituents as discussed above and in the following detailed description concerning the liquid composition can be included before the drying stage. Thus, e.g., a solid peroxide, e.g. in powder form, may be added to ensure a preserved and stable solution when the dried mucine preparation is dissolved in water.

The preferred artificial saliva composition of the invention, however, is a liquid composition of the concentration in which it is to be applied by the end user. For the preparation of a composition of this type containing one type of mucine, e.g., porcine gastric mucine, or a combination of two types of mucine, the dried mucine preparation is dissolved in preferably deionized water to a concentration corresponding to the desired viscosity of the product. The exact concentration desirable for a particular mucine preparation is easily found by preliminary experiments. When the mucine is porcine gastric mucine, the concentration will normally be in the range of 1–5% as mentioned above, but depending upon whether also other viscosity-building constituents such as carboxymethylcellulose are included, the range may be somewhat broader, e.g. 0.5–5%. To the solution, any other constituents to be included are added under gentle stirring to obtain complete solution. When a preservative is to be added to the liquid composition, this is preferably hydrogen peroxide which is added in a concentration of typically from about 1 millimol per liter to about 70 millimol per liter, preferably about 10–20 millimol per liter.

It has been found that a decrease in viscosity will take place during the sterilization treatment. A decrease in viscosity will also take place during the later storage and application period. At a concentraion of 4% of mucine, the viscosity will typically be in the range of 10-4 times that of water, as measured with an Oswald viscosimeter, the viscosity reducing towards the lower bound of this range during the final part of the storage period of 1–2 years.

The surface tension of the artificial saliva composition of the invention is preferably in the range of 40–60 dyn.cm.

A composition containing porcine gastric mucine in a concentration of 3–4% by weight together with ions of the types listed below has been found to have a surface tension of 50–52 dyn.cm, which is close to the surface tension of natural saliva. Furthermore, it has been found that the relationship between the polar and non-polar properties of a composition containing porcine gastric mucine may be adjusted to a less polar value by adding bovine salivary mucine which, at the same time, reduces the surface tension of the composition. Thus, a composition containing 2% of bovine salivary mucine has a surface tension of 44 dyn.cm and shows surprising non-polar properties.

A composition which contains procine gastric mucine and bovine salivary mucine in a proportion of 99:1 will show properties very close to natural saliva with respect to surface tension and the relationship between polar and non-polar properties. It has been found that a solution containing 4% of porcine gastric mucine and 0.1% of bovine salivary mucine has a proportion between polar and non-polar components corresponding to about equally pronounced polar and non-polar properties, which has also been found to be the balance prevailing under natural conditions in the mucosa.

In accordance with the above explanation, one aspect of the invention comprises a composition containing a combination of porcine gastric mucine and bovine salivary mucine. Preferably, such composition contains a preservative and optionally other constituents in accordance with the principles discussed above. The composition may be an aqueous solution or it may, like the peroxide-containing compositions of the present invention, be a dry composition for reconstitution into an aqueous solution.

The compositions of the invention which contain a combination of porcine gastric mucine and bovine salivary mucine may vary within wide ranges with respect to the ratio between the two types of mucine. Thus, the weight ratio between porcine gastric mucine and bovine salivary mucine in the composition may be from 1:1000 to 1000:1, depending on the desired properties of the composition with respect to surface tension, etc, in particular between 30:1 and 200:1, and preferably between 100:5 and 100:0.5 when the composition is an artificial saliva composition, although also the range between 15:3 and 15:1 is interesting for this purpose.

As examples of suitable liquid compositions of the invention may be mentioned the compositions illustrated in the below working example, and the following examples (all percentages being by weight):(1) An aqueous solution containing 1.0% of porcine gastric mucine, 0.2% of carboxymethylcellulose, and 0.02% of hydrogen peroxide, (2) an aqueous solution containing 0.5% of bovine salivary mucine, 1.0% of porcine gastric mucine, 0.04% of hydrogen peroxide, and 0.02% of KSCN, (3) an aqueous solution containing 2.0% of bovine gastric mucine, 0.01% of KCl, 0.08% of NaCl, 0.005% of $MgCl_2.6H_2O$, 0.02% of $CaCl_2.6H_2O$, 0.02% of KSCN, 0.035% of $K_2HPO_4$, and 0.03% of $H_2O_2$, (4) an aqueous solution containing 0.3% of bovine salivary mucine, 3.0% of porcine gastric mucine, 0.02% of hydrogen peroxide, 0.08% of NaCl, 0.005% of $MgCl_2.6H_2O$, 0.02% of $CaCl_2.6H_2O$, 0.02% of KSCN, 0.035% of $K_2HPO_4$, 2.0% of glycerine, 2 ppm NaF, (5) an aqueous solution corresponding to (4), but containing 0.1% of bovine salivary mucine and 4.0% of porcine gastric mucine, and (6) an aqueous solution corresponding to (4), but without any added bovine salivary mucine and optionally without NaF.

In the final stage, the solution is filtered to remove any particles remaining, e.g. through a filter having a pore size corresponding to Zeiss K5. The resulting solution is clear and "fresh" with a bacterial count below 10 and can be stored for more than 12 months at 4° C. in a container from which portions were withdrawn occasionally, such as once a day during a period of 2 months.

Examples of other constituents added to the composition are, apart from viscosity-building agents such as carboxymethylcellulose, enzymes of types which are present in human saliva, such as amylase, lysozyme, lactoperoxidase, etc. The enzymes and the hydrogen peroxide should be used in concentrations which are balanced in relation to each other.

EXAMPLE 1

From the preparation of pepsin described in U.S. Pat. No. 2,305,714, the supernatant liquid from which pepsin may be precipitated with alcohol is subjected to a precipitation by addition of 60% ethanol. To obtain a higher purity, the mucine precipitated (which corresponds with the NNR specifications (NNR=New and Non-official Remedies, ed. 1953, page 195)) is redissolved to a 10% solution in tap water at a temperature of 20°-25° C. by careful stirring with a slowly rotating blade stirrer. The dissolution and precipitation procedure (60% ethanol) is repeated until all peptones have been removed from the mucine (normally 3 times). Due to the gentle treatment, the resulting mucine is a mucine having a relatively high viscosity; when triturated with water, it yields a viscous, opalescent coloured solution. In dry state, the mucine is an almost white powder which is nearly odourless. The powder typically has the following data:

Mucine content: 73-94%
Ash (500° C.): max. 6.5%
Loss on drying (at 105° C.): max. 6.0%
Solubility: completely soluble in water
pH (2% solution): 3.7-6.5
Relative viscosity (2% sol. compared with water): 3.5-15
Total nitrogen: 6-9.9%
Nitrogen (alcohol extract): 6-9%
Reducing material (equivalent of dextrose): 15-35%
Heavy metals: less than 30 ppm.

This material is subjected to treatment with preservative ($H_2O_2$) in the following manner:

The mucine is dissolved as a 10% solution by addition of water at a temperature of about 20°-25° C. Per thousand liters of the solution, 1 liter of 30% $H_2O_2$ is added, and thereafter, the solution is allowed to stand for 2 hours to destroy bacterial and enzymatic activity and to remove any unpleasant taste from traces of peptones and fat.

Thereafter, the solution is spray-dried using an inlet air temperature of 220° C. and an outlet temperature of 160° C. The resulting spray-dried product has a bacterial count of less than 10 per g. An alternative drying procedure which is also suitable is freeze-drying or shelf drying.

The resulting dried product is subjected to a viscosity assay by preparing solutions containing 2, 3, 4, etc. percent by weight and measuring the viscosity of the solutions, using an Oswald viscosimeter. Normally, a 4% by weight solution will have an initial Oswald viscosity between 10 and 20 depending on the mucine used. In the present specific example, a 4% solution in deionized water shows a relative Oswald viscosity between 15 and 20.

To the solution of the mucine in deionized water, the following ingredients are added with gentle stirring.
Ingredients added per liter:
Mucine (prepared as described above): 45 g
KCl: 1.2 g
NaCl: 0.85 g
$MgCl_2.6H_2O$: 0.05 g
$CaCl_2.6H_2O$: 0.15 g
KSCN: 0.10 g
$K_2HPO_4$: 0.35 g
Flavouring agent: q.s.

To this composition may, if desired, be added NaF 2 ppm and/or sorbic acid 0.50 g.

The resulting solution might be used per se as a saliva substitute, but in order to obtain long-term stability even under conditions where the composition may occasionally be exposed to the surroundings, such as when a small portion thereof is withdrawn, a preservative is added, typically a 30% aqueous hydrogen peroxide solution to a concentration of 0.6 g per liter. Finally, the resulting solution is filtered through a K5 Zeiss filter and is packed in 1 or ½ liter bottles with screw caps having a small orifice for withdrawal of portions of the composition into multidose tubes.

Alternatively, the composition is filled directly into multidose tubes of 25 to 50 ml corresponding to 1 day's consumption, or it may be filled into aerosol containers of, e.g., 30 or 75 ml size.

As an other alternative, the solution of the invention may be incorporated as the liquid into a gum emulsified liquid package of the kind disclosed in U.S. Pat. No. 4,233,288, which package may contain up to 50% of the composition. The incorporation into the package is performed in analogy with the disclosure of the said U.S. patent. Also other emulsions may be formulated in which the solution of the invention is incorporated as one of the phases.

A composition prepared as described in Example 1, but additionally containing 30 g/liter sorbitol added together with the other constituents, was used for pilot study in 20 patients with severe xerostomia. The results were very encouraging, as all patients except one reported a much better sensation in the oral cavity, a feeling of relief and easiness during mastication and swallowing, and cessation of obstipation when using the composition.

Objectively, candidosis in 5 patients out of 7 with oral and pharyngial candidoses after 1-2 weeks of irrigation with the artificial saliva. The candidosis reappeared when the agent was discontinued.

EXAMPLE 2

In the composition of Example 1, the 4.5% of porcine gastric mucine were replaced with a combination of 3% porcine gastric mucine and 0.3% bovine salivary mucine in order to improve surface tension and non-polar properties. The mucines of this composition were analyzed (PGM=porcine gastric mucine; BSM=bovine salivary mucine):

|  | PGM | BSM |
|---|---|---|
| Protein | 43.9% | 57.6% |
| Sialic acid | 1.2% | 6.4% |
| Hexosamin | 16.0% | 6.2% |
| Hexose | 19.9% | 2.7% |

It appears from the above analyses that the combination of the two mucines may not only be of importance from a surface tension point of view, but also because of the fact that the ratio between the contents of the essential components sialic acid and hexosamine can be combined to a particular desired value by suitable combination of the two types of mucine. Instead of being supplied as aqueous solutions, the above-exemplified compositions could be supplied in dry form, with the same relative proportions between the components.

While the preceding discussion has primarily dealt with artifical saliva compositions, it is also within the scope of the present invention to provide compositions comprising a non-human mammalian buccal or gastrointestinal mucine for oral administration for other purposes, such as for relieving throat irritation or for acting as a carrier for medicaments to be supplied on mucous membranes in the mouth, including on the tongue, or in the throat. For such uses, the compositions will often be formulated to a somewhat higher viscosity then the viscosities which are preferred when the compositions are used as saliva substitutes. The uses of the compositions of the invention for oral administration of medicaments is especially interesting in connection with medicaments which, by the mucine content of the composition, are carried to, and retained on, the mucous membranes (or even to some extent penetrating into mucous membranes). When the mucine-containing compositions of the invention, possibly with somewhat higher viscosity than discussed above, are used for this purpose, the inherent medicament carrier-capabilities, and the mucines' capability of rendering the medicaments bio-available at mucous membranes, are utilized. Also the low surface tension of the mucines contribute to enhance the bio-availability of medicaments incorporated in such compositions. Apart from liquid compositions, also solid compositions which dissolve on sucking in the mouth, are contemplated mucine-containing compositions of the invention for oral use, for example, compositions for relieving irritations in the throat, or compositions where the mucine is associated with medicaments for treating the mouth or the throat. An example of such a medicament for oral administration is an antitussive, e.g., a composition containing 4% of porcine gastric mucine, 0.0007% of ephedrine, 0.0007% of ammonium chloride, and 0.02% of hydrogen peroxide, or a corresponding composition containing morphine.

Another main aspect of the application of the compositions of the invention is as compositions for nasal administration to human beings:

Many individuals suffer from dryness of the nose. By applying water to the nasal mucosa, only a brief moistening and relief is obtained. According to the present invention, sterilized and preservative-containing compositions comprising a non-human mammalian mucine selected from the group consisting of buccal and gastrointestinal mucines are used as nasal compositions for giving a relief and moistening of longer duration.

Compositions of the invention for use as nasal solutions are suitably composed in substantially the same manner as the oral compositions discussed above, the viscosity of the final composition when packed ready for use typically being of the order of 1–5, relative to water. The capability of the solution to properly moisten the nasal mucosa increases with decreasing surface tension of the composition, and hence, the low inherent surface tension of solutions containing mucines is of special value for this application. Another valuable property of the composition for this particular purpose is its capability to bind water to avoid dripping noses, e.g. with patients suffering from nasal catharr.

As examples of compositions of the invention for nasal application may be mentioned an aqueous solution containing 1% of porcine gastric mucine, 0.01% of hydrogen peroxide, 1% of glycerine, and flavouring agent q.s., e.g., mint oil. Instead of porcine gastric mucine, bovine salivary mucine may be used, e.g., in an amount of 0.3%, or a combination of porcine gastric mucine and bovine salivary mucine may be used, e.g., 0.5% of porcine gastric mucine and 0.2% of bovine salivary mucine.

The compositions of the invention for nasal application are prepared in the same manner as described above for the compositions for oral application, and again, hydrogen peroxide is the preferred preservative and is preferably used in the same concentrations as discussed above.

A further aspect of the application of the composition of the invention is as ophthalmic solution.

Ophthalmic solutions, that is solutions for the cleaning and care of contact lenses, are divided into two main types, that is, wetting solutions, and soaking and cleaning solutions. Wetting solutions are first discussed.

Contact lenses, in particular hard contact lenses, are hydrophobic (water repellent) and should be wetted before they are inserted into the eye. By the wetting, the following beneficial effects are obtained:
discomfort during insertion is minimized;
the optical performance is improved;
lens contamination during the insertion is prevented.

Wetting solutions should have the following properties:
they should show adequate wetting effect and such a viscosity that the solution adheres to the lens during insertion of the lens;
they should be sterile and self-sterilizing.

Conventional ophthalmic wetting solutions contain methyl cellulose as viscosity-building agent and polyvinyl alcohol as wetting agent in an isotonic solution containing sodium and potassium chloride. The solution is normally preserved with benzalkonium chloride.

According to this aspect of the present invention, a composition according to the invention, that is, an aqueous sterilized and preservative-containing solution of a non-human mammalian mucine selected from the group consisting of buccal and gastrointestinal mucines, is adapted for use as an ophthalmic wetting solution. An example of such a composition of the invention is a solution comprising an isotonic solution of a mucine with hydrogen peroxide incorporated as preservative. According to this aspect of the invention, the unique surface activity and viscosity properties of these mucines, combined with their other beneficial properties as discussed above, render them unique constituents of ophthalmic solutions meeting the above-mentioned requirements.

Depending upon the hydrophobic properties of the contact lenses to be treated with the solution, the mucine should be, e.g., a porcine gastric mucine or a bovine salivary mucine, or a combination thereof. Solutions of bovine salivary mucine which show more non-polar properties than solutions of gastric mucines should be selected for more hydrophobic lens types. In accordance with what has been described above, the mucine in the composition also functions as a viscosity-imparting agent in the ophthalmic solutions of the present invention.

As explained above, hydrogen peroxide, when used as both the sterilizing principle and as the preservative present in the final solution, will decrease in concentration with time. As a hydrogen peroxide concentration of 50 ppm and less is presumed to be a tolerable, physiologically acceptable concentration of hydrogen peroxide in ophthalmic solutions which come into direct contact with the eye, the composition of the invention, when used for this purpose, may be sterilized by adding hydrogen peroxide to an initial concentration of about 100 ppm, which concentration will, already after about one week, have decreased to about 50 ppm and less and must be presumed to be in the range of 50 to 5 ppm at least one year later, still with the surprising preserving effect yielding the sterility which is characteristic of compositions of the invention containing hydrogen peroxide as preservative.

Ophthalmic soaking and cleaning solutions will now be discussed:

On withdrawal from the eye, a contact lens should be stored in a soaking solution which exerts the following functions:

It prevents any ocular secretion remaining on the lens from solidifying or even hardening.

It sterilizes the lens and maintains its sterility.

It maintains the hydrated equilibrium of the lens while it is not being worn.

Like the wetting solution, a typical soaking solution contains an antibacterial agent, but often in a higher concentration than in the wetting solution. The typical soaking solution also usually contains a solubilizing agent to loosen any residues attaching to the lens, and distilled water. Normally, the lens is rinsed in cold water after being withdrawn from the soaking solution.

According to the present aspect of the invention, the above-described type of sterilized, preservative-containing mucine solution which constitutes a suitable ophthalmic wetting solution for a given type of contact lens, also constitutes a suitable soaking solution for the same type of contact lens, due to the unique sterile and sterilizing properties of the composition, and because the mucine in itself has properties which permits it to function as a solubilizing and cleaning agent.

Thus, according to this aspect of the invention, the system comprising mucine and a concentration of hydrogen peroxide which is sufficiently low to allow the introduction of the composition into contact with the eye epithel, while still being sufficiently high to warrant the sterilizing properties of the system, opens the possibility of establishing a combined ophthalmic solution which combines the properties and functions of both the wetting solution type and the soaking and cleaning type of ophthalmic solution.

Due to their unique properties, compositions of this type and with viscosities, isotonic properties, and surface tension properties suitably adapted, may also be used as solutions for application on the eye for other purposes than in connection with contact lenses.

As will be understood on the background of the above explanation and as appears from the claims, separate novel aspects of the present invention comprise a sterilized composition comprising a non-human mammalian mucine selected from the group consisting of buccal and gastro-intestinal mucines and containing an oxidizing bactericide, especially a peroxide, in particular hydrogen peroxide, as a preservative. The said composition will preferably show the features discussed above and may be an aqueous solution as discussed above, or it may be a dry composition for reconstitution. Another novel aspect of the invention is a composition comprising a combination of porcine gastric mucine and bovine salivary mucine. A third aspect of the invention comprises a method for sterilizing mucine-containing aqueous compositions by adding an oxidizing bactericide, in particular a peroxide such as hydrogen peroxide, thereto. In this aspect, the hydrogen peroxide is suitably added to a concentration of about 100-300 ppm, such as a concentration of about 250 ppm.

From the above discussion, it will be understood that the compositions of the invention, due to the unique properties of the mucines and combinations thereof for the particular purposes stated or for other purposes where a physiologically tolerable surfactant is desirable, constitute very valuable products, especially when they are sterilized and preserved by means of hydrogen peroxide which, as explained above, shows a surprisingly beneficial combination of properties in that it is capable of effectively sterilizing and preserving the compositions when used in such low concentrations that it does not in any way interfere with the use of the compositions for application on even very sensitive human mucous membranes.

French Patent Specification No. 3.554 M discloses mucine-containing compositions for treatment of human mucous membranes and discloses examples of such compositions for, e.g., treatment of infections in nose or mouth. The disclosure of this French specification does not teach how one could sterilize and preserve—in a manner which would be physiologically tolerable with respect to the application of the compositions of the present invention—a mucine-containing solution so as to ensure that the solution will remain stable and bactericidal under the conditions which are fulfilled by the compositions of the present invention.

We claim:

1. An aqueous mucine-containing composition, in particular for application to human mucous membranes and/or for use as an ophthalmic solution, comprising a non-human mammalian mucine selected from the group consisting of buccal and gastrointestinal mucines, the composition having a viscosity of at the most 50 relative to water, as measured with an Oswald viscosimeter, said composition being sterilized and containing an oxidizing bactericide preservative which is present in a physiologically tolerable concentration with respect to the application of the composition.

2. A composition as claimed in claim 1 which is substantially free from any mucine-decomposing enzymatic activity.

3. A composition as claimed in claim 1 or 2, in which the bacterial count of the composition remains substantially constant for a period of at least one year when the composition is kept in a closed container at room temperature.

4. A composition as claimed in claim 3 in which the bacterial count of the composition remains substantially constant when the composition is kept at 4° C. in a container from which a portion of the solution is withdrawn occasionally during a period of two months.

5. A composition as claimed in claim 1 in which the oxidizing bactericide preservative is a peroxide.

6. A composition as claimed in claim 1 in which the oxidizing bactericide preservative is present in a concentration of about 0.01-70 millimol per liter.

7. A composition as claimed in claim 6 wherein the oxidizing bactericide preservative is hydrogen peroxide and is present in an initial concentration of about 10 millimol per liter.

8. A composition as claimed claim 1 or 2 in which the mucine is porcine gastric mucine and/or bovine salivary mucine.

9. A composition as claimed in claim 8 in which the mucine is a combination of porcine gastric mucine and bovine salivary mucine.

10. A composition as claimed in claim 9 wherein the weight ratio between porcine gastric mucine and bovine salivary mucine in the composition is from 1:1000 to 1000:1.

11. A composition as claimed in claim 10 wherein the weight ratio between porcine gastric mucine and bovine salivary mucine is between 30:1 and 200:1.

12. A composition as claimed in claim 11 wherein the weight ratio between porcine gastric mucine and bovine salivary mucine is in the range between 100:5 and 100:0.5.

13. A composition as claimed in claim 1 or 11 in which the mucine content of the solution is 0.2-6% by weight.

14. A composition as claimed in claim 13 in which the mucine content of the solution is 1-5% by weight.

15. A composition as claimed in claim 8 for use as an artifical saliva solution, the composition having a viscosity between 2 and 30 relative to water, as measured with an Oswald viscosimeter.

16. An artificial saliva solution as claimed in claim 15 which has a viscosity between 4 and 10.

17. An artificial saliva solution as claimed in claims 16 which contains at least one ion species found in human saliva.

18. An artificial saliva solution as claimed in claim 17 which contains a thiocyanate.

19. An artificial saliva solution as claimed in claim 18 in which the thiocyanate is present in a concentration of from 0.25 mM to 6 mM.

20. An artificial saliva solution as claimed in claim 16 which has a surface tension in the range between 40 and 60 dyn.cm.

21. A sterilized composition comprising a non-human mammalian mucine selected from the group consisting of buccal and gastrointestinal mucines and containing an oxidizing bactericide, as a preservative.

22. A composition as claimed in claim 21 which comprises porcine gastric mucine.

23. A composition as claimed in claim 21 which comprises bovine salivary mucine.

24. A composition as claimed in claim 21 which contains a combination of porcine gastric mucine and bovine salivary mucine.

25. A composition as claimed in claim 24 wherein the weight ratio between porcine gastric mucine and bovine salivary mucine in the composition is from 1:1000 to 1000:1.

26. A composition as claimed in claim 25 wherein the weight ratio between porcine gastric mucine and bovine salivary mucine is between 30:1 and 200:1.

27. A composition as claimed in claim 26 wherein the weight ratio between porcine gastric mucine and bovine salivary mucine is in the range between 100:5 and 100:0.5.

28. A composition as claimed in claim 25 which is an aqueous solution.

29. A composition as claimed in claim 25 which is a dry composition.

* * * * *